US010675174B2

(12) United States Patent
Castillo (10) Patent No.: US 10,675,174 B2
(45) Date of Patent: *Jun. 9, 2020

(54) BREATHING SYSTEM

(71) Applicant: James D. Castillo, Los Alamos, CA (US)

(72) Inventor: James D. Castillo, Los Alamos, CA (US)

(*) Notice: Subject to any disclaimer, the term of this patent is extended or adjusted under 35 U.S.C. 154(b) by 246 days.

This patent is subject to a terminal disclaimer.

(21) Appl. No.: 15/016,087

(22) Filed: Feb. 4, 2016

(65) Prior Publication Data

US 2016/0151194 A1 Jun. 2, 2016

Related U.S. Application Data

(60) Division of application No. 14/622,448, filed on Feb. 13, 2015, now Pat. No. 9,283,106, which is a continuation-in-part of application No. 14/502,348, filed on Sep. 30, 2014, now Pat. No. 9,675,493.

(60) Provisional application No. 61/918,826, filed on Dec. 20, 2013, provisional application No. 61/937,018, filed on Feb. 7, 2014.

(51) Int. Cl.
*A61F 5/08* (2006.01)
(52) U.S. Cl.
CPC .................................... *A61F 5/08* (2013.01)
(58) Field of Classification Search
CPC .......................................................... A61F 5/08
USPC ................................... 606/199, 201, 204.45
See application file for complete search history.

(56) References Cited

U.S. PATENT DOCUMENTS

| 3,835,848 | A | 9/1974 | Berner |
|---|---|---|---|
| 4,835,506 | A | 5/1989 | Leupold |
| 4,886,349 | A | 12/1989 | Willis |
| 5,533,503 | A | 7/1996 | Doubek et al. |
| 5,566,503 | A | 7/1996 | Doubek et al. |
| 5,719,655 | A | 2/1998 | Peschel et al. |
| 5,913,873 | A | 6/1999 | Blach et al. |
| 5,957,126 | A | 9/1999 | Neeser |
| 6,006,746 | A | 12/1999 | Karell |
| 6,033,422 | A | 3/2000 | Blach et al. |

(Continued)

FOREIGN PATENT DOCUMENTS

| CN | 1389185 | 1/2003 | |
|---|---|---|---|
| EP | 0855175 A1 * | 7/1998 | ............... A61F 5/08 |

(Continued)

OTHER PUBLICATIONS

International Search Report and Written Opinion of International Application No. PCT/US15/67530, dated May 16, 2016, 11 pages.

(Continued)

*Primary Examiner* — Vy Q Bui
(74) *Attorney, Agent, or Firm* — Stetina Brunda Garred and Brucker (57) ABSTRACT

A breathing system is provided which enhances the ability of a user to breathe through the user's nasal passageways. The breathing system generally includes a bridge member and a pair of nasal appliques which are attachable to the lateral portions of the user's nose. The bridge member is positionable adjacent the appliques to activate the system and impart a dilating force onto the user's nose. The system may be deactivated by removing the bridge member from the appliques, and thereby removing the dilating force from the user's nose.

18 Claims, 7 Drawing Sheets

(56) References Cited

U.S. PATENT DOCUMENTS

| | | |
|---|---|---|
| 6,352,548 B1 | 3/2002 | Blach et al. |
| 6,533,415 B2 | 3/2003 | Wang et al. |
| 6,540,349 B1 | 4/2003 | Liesegang |
| 6,648,471 B1 | 11/2003 | Dalrymple et al. |
| 6,676,681 B1 | 1/2004 | Blach et al. |
| 6,823,864 B2 | 11/2004 | Blach et al. |
| 7,091,634 B2 | 8/2006 | Yi et al. |
| 7,118,210 B2 | 10/2006 | Landers |
| 7,793,661 B2 * | 9/2010 | Macken ............ A61F 5/56 128/846 |
| D639,762 S | 6/2011 | Brogden et al. |
| D644,324 S | 8/2011 | Brunner et al. |
| D644,325 S | 8/2011 | Brunner et al. |
| 8,042,542 B2 | 10/2011 | Ging et al. |
| 8,292,427 B2 | 10/2012 | Zelazowski |
| 8,459,254 B1 | 6/2013 | Jassir et al. |
| D696,400 S | 12/2013 | Brogden et al. |
| D701,957 S | 4/2014 | Brunner et al. |
| D703,318 S | 4/2014 | Brunner et al. |
| 2002/0029408 A1 | 3/2002 | Lindahl |
| 2003/0000521 A1 | 1/2003 | Beaudry |
| 2007/0105824 A1 | 5/2007 | Erickson-Miller et al. |
| 2007/0252946 A1 | 11/2007 | Welchel |
| 2008/0097517 A1 | 4/2008 | Holmes et al. |
| 2008/0119885 A1 | 5/2008 | Yazdi |
| 2009/0183734 A1 | 7/2009 | Kwok et al. |
| 2009/0188023 A1 | 7/2009 | Hsu |
| 2010/0309425 A1 | 12/2010 | Zelazowski |
| 2011/0000483 A1 | 1/2011 | Matthias et al. |
| 2012/0024639 A1 | 2/2012 | Castro |
| 2012/0036607 A1 | 2/2012 | Beliveau |
| 2012/0172923 A1 | 7/2012 | Fenton et al. |
| 2014/0296904 A1 | 10/2014 | Andre |
| 2014/0375946 A1 | 12/2014 | Rochford et al. |
| 2015/0001014 A1 | 1/2015 | Noborio et al. |
| 2015/0173933 A1 | 6/2015 | Castillo |
| 2015/0173934 A1 | 6/2015 | Castillo |
| 2016/0193070 A1 | 7/2016 | Castillo |
| 2017/0106222 A1 | 4/2017 | Mayer et al. |

FOREIGN PATENT DOCUMENTS

| | | |
|---|---|---|
| JP | H10192412 | 7/1998 |
| JP | 2009-535079 | 10/2009 |
| KR | 200404740 | 12/2005 |
| WO | WO2002/003125 | 1/2002 |

OTHER PUBLICATIONS

International Search Report and Written Opinion of International Application No. PCT/US2016/022637, dated Jun. 9, 2016, 10 pages.
International Search Report and Written Opinion for International Application No. PCT/US14/69817, dated Mar. 11, 2015, 11 pages.
Australian Government IP Australia, Examination report No. 1 for standard patent application, Oct. 24, 2017, 5 pages.
Office Action for corresponding Japanese Patent Application No. 2016-560622 with English translation, dated Nov. 1, 2017, 5 pages.
International Search Report and Written Opinion for International Application No. PCT/US 17145688, Oct. 31, 2017, 11 pages.
First Office Action of CN Application 201480075735.9, dated May 2, 2017, 9 pages.
Summary of First Office Action of CN Application 2014800757359, dated May 2, 2017, 5 pages.
European Patent Office, extended European search report for Application No. EP 14871764, dated Jul. 7, 2017, 10 pages.
Patent Cooperation Treaty, International Preliminary Report on Patentability for Application No. PCT/US16/22637, dated Aug. 3, 2017, 9 pages.
Patent Cooperation Treaty, International Search Report and Written Opinion for International Application No. PCT/US2018/066312, dated Mar. 5, 2019, 12 pages.

* cited by examiner

BREATHING SYSTEM

CROSS-REFERENCE TO RELATED APPLICATIONS

This application is a divisional of U.S. patent application Ser. No. 14/622,448, filed Feb. 13, 2015, which is a continuation-in-part of U.S. patent application Ser. No. 14/502,348, filed Sep. 30, 2014, which claims the benefit of U.S. Provisional Application No. 61/918,826, filed Dec. 20, 2013, and U.S. Provisional Application No. 61/937,018, filed Feb. 7, 2014, the contents of each of the foregoing applications being expressly incorporated herein by reference.

STATEMENT RE: FEDERALLY SPONSORED RESEARCH/DEVELOPMENT

Not Applicable

BACKGROUND OF THE INVENTION

1. Field of the Invention

The present invention relates generally to a breathing system, and more specifically to a breathing system designed to enhance nasal airflow for the user by urging the user's nostrils to a more open position, wherein the breathing system may optionally be used with an optical lens as a stabilizing mechanism for the lens.

2. Description of the Related Art

It is readily understood that breathing is important when playing sports or taking part in physical competition due to the increased demand for oxygen by the body. Breathing may be achieved by drawing air into the body through an individual's nostrils and/or through the individual's mouth. However, in some instances, it is preferable to breathe almost exclusively through the nostrils, as there may be a downside to breathing through one's mouth. Along these lines, breathing through the mouth may lead to rapid water loss and heat loss, both of which increase the likelihood of exercise-induced asthma. Exclusive breathing through the mouth may also lead to an increased heart rate, hyperventilation and reduced athletic ability.

It is also understood that eyewear is commonly used when participating in many sports and activities. Such eyewear may include protective eyewear, or vision-enhancing (e.g., prescription) eyewear. For instance, goggles are readily worn by many athletes participating in snowboarding, skiing, motocross, automotive racing, basketball, baseball, hockey, etc. Goggles are typically configured such that a portion of the goggle frame extends over the user's nose, and thus, goggles may impact one's ability to breathe through the user's nasal passage.

Moreover, many goggles are fitted with a foam liner which interfaces with the user's face to create a barrier or seal which prevents snow, rain, dirt or other debris from entering the goggles and creating a potential irritant in the user's eye. In order to create an effective seal or barrier around the goggles, the goggles are compressed against the user's face, typically through the use of an elastic band which is worn around the head. The compression of the foam liner against the user tends to compress the nasal passages of the user, which further inhibits the ability of the user to breathe through the nose.

In view of the foregoing drawbacks associated with conventional goggles, Applicant has developed a goggle breathing system directed toward alleviating the pressure on the nostrils and improving the user's ability to breathe when wearing goggles. More information regarding Applicant's goggle breathing system can be found in U.S. patent application Ser. No. 14/502,348, entitled Goggle Breathing System.

However, in some instances, eyewear or goggles are not worn by the user. For instance, sports such as basketball, baseball, soccer, running, volleyball, hockey, and skateboarding typically do not require the use of goggles or other eyewear. However, there remains a need for enhancing one's ability to breathe.

Accordingly, there is a need in the art for a device specifically adapted for enhancing the user's ability to breathe through the user's nasal passage. Various aspects of the present invention address this particular need, as will be discussed in more detail below.

BRIEF SUMMARY OF THE INVENTION

In accordance with one embodiment of the present invention, there is provided a breathing system which enhances the ability of a user to breathe through the user's nasal passageways. Various embodiments of the breathing system do not require the use of goggles or other eyewear. Rather, the breathing system generally includes a bridge member and a pair of nasal appliques which are attachable to the lateral portions of the user's nose. The bridge member is positionable adjacent the appliques to activate the system and impart a dilating force onto the user's nose. The system may be deactivated by removing the bridge member from the appliques, and thereby removing the dilating force from the user's nose. The dilating force may be selectively turned ON and OFF. The dilating effect may be most noticeable when the bridge member is first applied. This may allow the user to have the advantage only when engaged in the activity for which the user is using the breathing system.

According to one embodiment, the breathing system includes a bridge member having a pair of distal portions and a middle portion positioned between the pair of distal portions. The bridge member is configured to be positionable adjacent the user's nose, with each distal portion residing adjacent a respective lateral region of the user's nose. A pair of nasal appliques are adapted to be attachable to the respective lateral regions of the user's nose, with each nasal applique being magnetically attractable to respective ones of the pair of distal portions. The attraction between the pair of nasal appliques and the bridge member impart a dilating force on the user's nose to dilating the nasal passage.

Each nasal applique may include a flexible base layer including a first surface and an opposing second surface. The first surface may include an adhesive disposed thereon to enable the first surface to be selectively attachable to the nose of the user. A metallic element may be coupled to the second surface of the base layer. The bridge member may include a main body and a pair of magnets coupled to the main body at respective ones of the distal portions of the bridge member. The metallic element in each nasal applique may be magnetically attractable to a respective one of the pair of magnets.

The bridge member may include a first surface and an opposing second surface, the first surface facing toward the user's nose and the second surface facing away from the user's nose when the bridge member is positioned adjacent the user's nose. A pair of spacers may extend from the first surface and away from the second surface, with each spacer being positioned at a respective one of the pair of distal portions. The spacers may be integrally formed with the main body.

The bridge member may be substantially inflexible.

The bridge member may be configured to be selectively flexible between a neutral position and a flexed position. The bridge member may be configured to substantially remain in the flexed position once transitioned thereto. The bridge member may include at least one flexible member and a pair of distal members coupled to opposed ends of the at least one flexible member. The at least one flexible member may be selectively bendable to place the bridge member in a prescribed orientation. The bridge member may be biased toward the neutral position.

The bridge member may include a flexible band and a pair of distal members coupled to opposed ends of the flexible band. The flexible band may be bendable between neutral and flexed positions, with the band being biased toward the neutral position.

The bridge member may be adapted to be attachable to eyewear, such as a lens. The bridge member may be configured to stabilize or support the lens on the face of the user.

According to another embodiment, there is provided a breathing system including a pair of nasal appliques configured to be attachable to an outer surface of a user's nose adjacent a user's nostrils. A bridge member is configured to be selectively positionable adjacent the nose of the user and to interact with the pair of nasal appliques. The pair of nasal appliques and the bridge member are configured to selectively transition between an ON state wherein the pair of nasal appliques interact with the bridge member to apply a dilating force on the nose of the user, and an OFF state wherein the bridge member is moved away from the pair of nasal appliques to cease application of the dilating force on the nose of the user.

The present invention will be best understood by reference to the following detailed description when read in conjunction with the accompanying drawings.

BRIEF DESCRIPTION OF THE DRAWINGS

These and other features and advantages of the various embodiments disclosed herein will be better understood with respect to the following description and drawings, in which.

Common reference numerals are used throughout the drawings and the detailed description to indicate the same elements.

DETAILED DESCRIPTION OF THE INVENTION

The detailed description set forth below in connection with the appended drawings is intended as a description of certain embodiments of a breathing system and is not intended to represent the only forms that may be developed or utilized. The description sets forth the various structure and/or functions in connection with the illustrated embodiments, but it is to be understood, however, that the same or equivalent structure and/or functions may be accomplished by different embodiments that are also intended to be encompassed within the scope of the present disclosure. It is further understood that the use of relational terms such as first and second, and the like are used solely to distinguish one entity from another without necessarily requiring or implying any actual such relationship or order between such entities.

Referring now to the drawings, wherein the showings are for purposes of illustrating preferred embodiments of the present invention only, and are not for purposes of limiting the same, there is depicted several embodiments of breathing system for enhancing the ability of a user to breathe through the user's nose by opening the user's nasal passageways. As will be described in more detail below, the embodiments depicted in FIGS. 1-33 are specifically configured and adapted to interface with the user's nose without relying upon eyewear, such as glasses, goggles, or the like, to support the breathing system on the user's nose. However, in the event the user does wear a lens, such as a prescription lens, uv-protective lens, or other lens, other embodiments are specifically configured and adapted to interface with such a lens, specifically the embodiment depicted in FIGS. 34 and 35.

Various aspects of the present invention are directed toward imparting a dilating force on the user's nose to open the user's nasal passageways. Along these lines, the anatomy of the human nose 10 generally includes a nasal ridge 12, a pair of nasal passageways 14, which are separate by a nasal septum 16. The nose 10 also includes skin extending over the lateral regions 18 (see FIGS. 1 and 2) thereof, which may be referred to as the "ala of the nose." The dilating force is applied on the lateral regions 18 of the nose 10 to cause the lateral regions 18 to flare outwardly, thereby increasing the volume of the nasal passageways 14.

Referring now specifically to FIGS. 1-9, there is depicted a first embodiment of a breathing system 20 which generally includes a bridge member 22 and a pair of nasal appliques 24. The bridge member 22 includes an arcuate main body 26 having a concave inner surface 28 and an opposing convex outer surface 30. The main body 26 includes a middle portion 32 defining an apex which is located between two distal portions 34, wherein each distal portion terminates 34 at a respective distal tip 36. The two distal tips 36 are spaced from each other by a distance, $D_1$ which allows the bridge member 22 to fit over the user's nose 10, with the distal portions 34 being positioned adjacent opposing lateral regions 18 of the user's nose 10. The bridge member 22 may be fabricated in various sizes to accommodate differently sized noses. Along these lines, the distance $D_1$ may be anywhere from 1.0 inch for use on a small nose (e.g., for a child), to over 2.5 for use on a larger nose. For an average nose, the distance $D_1$ may be approximately equal to 1.75 inches.

The main body 26 includes a pair of opposed longitudinal edges 38 (see FIG. 5) and a pair of opposed transverse edges 40, which essentially define the aforementioned distal tips 36. The distance between the opposed longitudinal edges 38 defines a bridge member thickness, $T_1$, which may be equal to approximately 0.5 inches, although other thickness dimensions may be used without departing from the spirit and scope of the present invention.

The main body 26 is rigidly formed so as to substantially maintain its shape. Along these lines, the main body 26 is preferably more resistant to bending, or flexing than is the skin of the user's nose 10. In this respect, the main body 26 is capable of being disposable in compression, that is to say, the main body 26 is capable of having a force applied thereto.

The bridge member 22 further includes a plurality of magnets 42 coupled to the concave inner surface 28 adjacent the distal portions 34 of the main body 26. In the exemplary embodiment, the bridge member 22 includes a pair of magnets 42 at each distal portion 34. The magnets 42 may be received within a cavity or recess formed within the main body 26 that is substantially complimentary in shape and size to the pair of magnets 42. The magnets 42 may be adhered or otherwise coupled to the main body 26 using fastening mechanisms known by those skilled in the art.

The nasal applique 24 includes a metallic element 44, preferably a ferrous metal, that is captured between a base layer 46 and an cover layer 48. It is understood that the cover layer 48 is optional, as there may be other embodiments wherein the metallic element 44 is coupled to the base layer 46, with the metallic element 44 being uncovered. The metallic element 44 includes a first surface which interfaces with the base layer 46 and a second surface which interfaces with the cover layer 48. According to one embodiment, the second surface defines a convex, arcuate, or "domed" configuration, to facilitate contact with the magnets 42 without flat-to-flat attachment, which may create uncomfortable torque on the user's nose 10. As alluded to above, it is understood that the dual-layer design is optional, and that in other embodiments, the nasal applique 24 may comprise a single layer with the metallic element 44 coupled to the single layer. In this regard, the metallic element 44 may be position on an upper surface of the single layer, wherein the single layer resides between the metallic element 44 and the user when the applique 24 is applied to the user's nose. Alternatively, the metallic element 44 may be positioned on a lower surface of the single layer, such that the metallic element 44 resides between a portion of the single layer and the user's nose during use. It is also contemplated that the metallic element 44 may be encapsulated or captured within that single layer.

The base layer 46 includes an inner surface and an opposing outer surface. The inner surface is adapted to engage with the metallic element 44 and the cover layer 48, while the outer (lower) surface is adapted to engage with the user's nose 10. The outer (lower) surface may be coated with an adhesive to allow the base layer 46 to be adhered to the user's nose 10. A tear-away layer (not shown) may extend over the outer surface to preserve the adhesive until the nasal applique 24 is applied to the user's nose 10. The cover layer 48 also includes an inner surface and an opposing exposed surface. The inner surface of the cover layer 48 is adapted to interface with the metallic element 44 and the base layer 46, while the exposed surface of the cover layer 48 is adapted to engage with the magnets 42 of the bridge member 22.

The preferred peripheral contour of the nasal applique 24 is an hour-glass like configuration, having two enlarged end portions and a narrow middle portion, with the metallic element 44 being located at the narrow middle portion. The narrow middle portion is defined by a pair of opposed cutouts. When the nasal applique 24 is applied to the nose, the cutouts are placed over the crease on the user's nose that extends generally around a flared nostril. This provides a cutout around the crease, which becomes very active when breathing. Having that portion of the nose uncovered allows for dilating and breathing motion without initiating peeling of the applique 24. The opposed cutouts allow for use of the applique 24 on either side of the user's nose. However, it is also contemplated that the applique 24 may be specifically formed for use on only one side of the nose, and thus, such appliques 24 may only have one cutout.

It is contemplated that the nasal appliques 24 may have logos, trademarks, or other indicia emblazoned thereon. The indicia may be emblazoned on the base layer 46 and/or the cover layer 48.

According to one embodiment, the base layer 46 and cover layer 48 are both configured to extend radially outward beyond the outer periphery of the metallic element 44 to define a peripheral ring portion 50. As such, the metallic element 44 is positioned over a central region of the base layer 46 and is surrounded by a peripheral region of the base layer 46. In the exemplary embodiment, depicted in FIG. 9, the outer peripheries of the cover layer 48 and the base layer 46 are substantially equal. However, it is understood that prior to being joined to the metallic element 44 and base layer 46, the cover layer 48 may define a peripheral dimension that is larger than the base layer 46 so as to accommodate the thickness of the metallic element 44.

In order to use the breathing system 20, the user first applies the nasal appliques 24 to both sides of the user's nose 10. If the outer surface of the base layer 46 is covered by a tear-away layer, the user removes the tear-away layer to expose the adhesive. The user then places a first nasal applique 24 on a first lateral region 18 (e.g., the ala of the nose) adjacent a first nostril opening 14, and a second nasal applique 24 on a second lateral region 18 adjacent a second nostril opening 14. Typically, the appliques 24 are placed on the nose near the transition of the nose bone.

Once both nasal appliques 24 are applied to the respective lateral regions 18 of the nose 10, the user may place the bridge member 22 over the nose 10, with the magnets 42 on the bridge member 22 being placed adjacent respective ones of the nasal appliques 24 to allow the metallic elements 44 in the nasal appliques 24 to be magnetically drawn to the magnets 42 in the bridge member 22. The interaction between the metallic elements 44 and the magnets 42 creates dilating forces which are imparted to the respective lateral regions 18 of the nose 10 via the interconnection of the nasal appliques 24 to the nose 10. The dilating forces urge the lateral regions 18 of the nose 10 outward, which increases the size of the nasal passageways 14 to enhance the user's ability to breathe. The bridge member 22 substantially retains its shape as it is placed over the user's nose 10, despite the increased magnetic attraction between the magnets 42 and the metallic elements 44. Along these lines, the bridge member's resistance to bending or flexing causes the lateral regions 18 of the nose to be drawn to the bridge member 22, rather than the bridge member 22 being drawn to the nose 10.

Furthermore, the central positioning of the metallic element 44 relative to the underlying base layer 46 causes the central portion of the base layer 46 to be pulled toward the magnet 42 when the magnet 42 is placed adjacent the metallic element 44. The centrally applied force on the base layer 46 creates a shear force between the base layer 46 and the user's nose 10. In this respect, although the magnetic attraction between the magnet 42 and the metallic element 44 pulls the metallic element 44 along an axis extending between the magnet 42 and the metallic element 44, the generally central location of the metallic element 44 within the applique 24 distributes a portion of the force created by the attraction of the metallic element 44 in the applique 24 and the positioned magnets 42 to the compliant area around the metallic element 44 which substantially translates the force to shear in a plane along the skin of the user's nose, which is generally offset from the axis extending between the magnet 42 and the metallic element 44, and in some instances, may be perpendicular to such axis. The shear component allows for a much more aggressive dilation compared to systems that pull generally perpendicularly to the skin, as the adhesives are much stronger in shear.

The bridge member 22 remains on the user's nose 10 as long as the user desires. Along these lines, the bridge member 22 is specifically configured and adapted to allow the user to compete in a sporting event or other activities with the bridge member 22 coupled to the user's nose 10. In this respect, the attraction between the magnets 42 and the metallic elements 44 is strong enough to maintain the bridge member 22 in place while the user participates in such events or activities under normal circumstances and impact.

One particular advantage of the breathing system 20 is the ability of the system 20 to selectively transition between an ON (engaged) state and an OFF (disengaged) state without removing the nasal appliques 24 from the user's nose 10. In the ON state, the nasal appliques 24 are applied to the user's nose 10, and the bridge member 22 is engaged with the nasal appliques 24, which results in the dilating force being imparted on the user's nose 10. The breathing system 20 may transition from the ON state to the OFF state by disengaging the bridge member 22 from the nasal appliques 24, which stops the application of the dilating force on the user's nose 10. In this regard, when the system 20 is in the OFF state, the system 20 is inactive. If the user subsequently wants to turn the system 20 back ON, the user simply re-applies the bridge member 22 over the nose 10 and into engagement with the nasal appliques 24.

The ability to selectively transition the system 20 between ON and OFF states may be particularly advantageous, particularly when participating in sports-related activities, where the user may take breaks from time-to-time. For instance, many sports relates activities are divided into heats, periods, quarters, halves, etc., such that the user experiences extended periods of inactivity between extended active periods. The user may want to transition the system 20 to the OFF state during periods of inactivity, and to the ON state during periods of activity. The configuration of the nasal appliques 24 and the associated bridge member 22 allows for such quick and easy transition to give the user the enhanced ability to breathe when needed during the active periods. The selective transition of the system 20 between an ON state and an OFF state may be analogous to a quarterback taking his mouthpiece out between plays.

Referring now to FIGS. 10-17, there is depicted a second embodiment of a breathing system. The breathing system includes a bridge member 122 and a pair of nasal appliques 24. The primary distinction between the first and second embodiments is the inclusion of a spacer 125 on the bridge member 122 for spacing the magnets 142 farther from the nasal appliques 24 to enhance the dilating force (e.g., the nasal appliques 24 are pulled farther). In this respect, the nasal appliques 24 used in the second embodiment are similar to the nasal appliques 24 discussed above in connection with the first embodiment. Thus, the following discussion will focus on the unique configuration of the bridge member 122.

Figure 1:
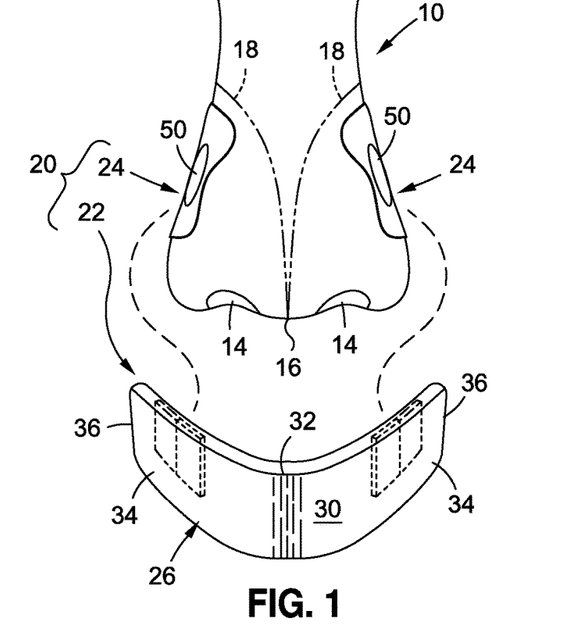
FIG. 1 is an upper perspective view of a breathing system constructed in accordance with a first embodiment of the present invention, the breathing system including a pair of nasal appliques and a bridge member which interacts with the nasal appliques.
Figure 2:
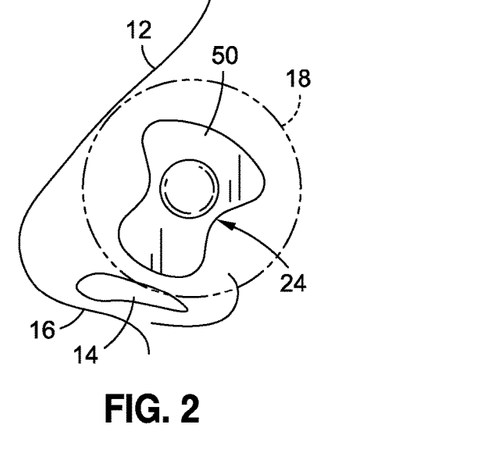
FIG. 2 is a side view of a nasal applique applied to a lateral region of a user's nose.
Figure 3:
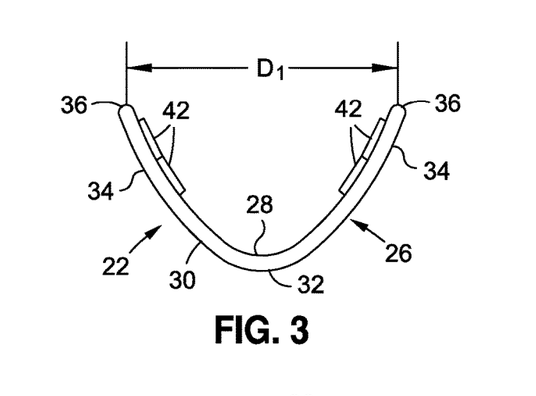
FIG. 3 is a top view of the bridge member depicted in FIG. 1.
Figure 4:
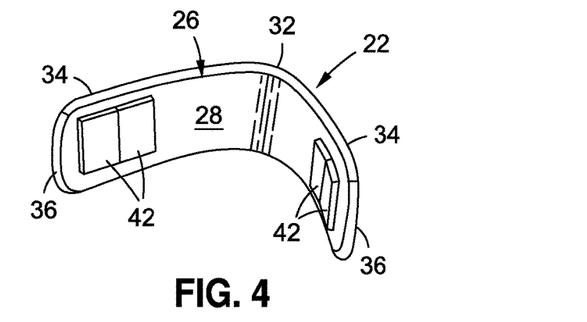
FIG. 4 is a rear perspective view of the bridge member depicted in FIG. 1.
Figure 5:
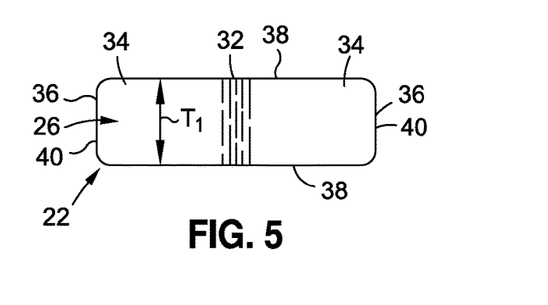
FIG. 5 is a front view of the bridge member depicted in FIG. 1.
Figure 6:
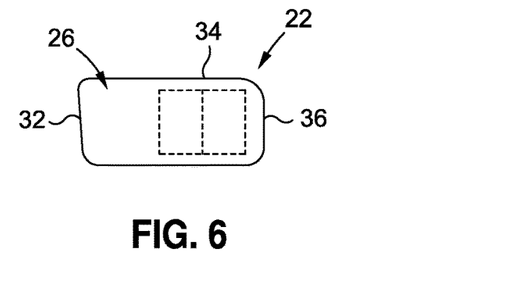
FIG. 6 is a side view of the bridge member depicted in FIG. 1.
Figure 7:
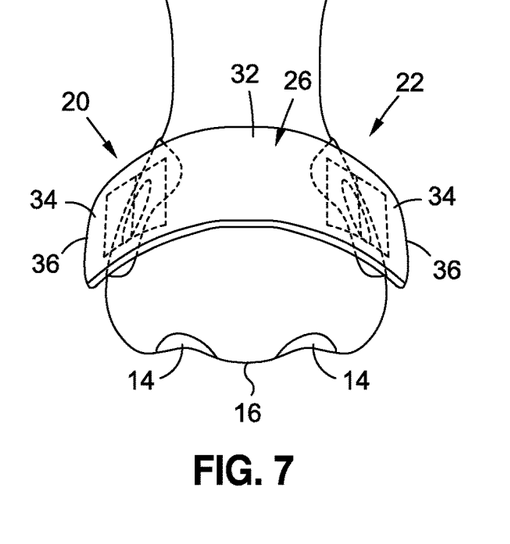
FIG. 7 is an upper perspective view of the bridge member engaged with the pair of nasal appliques (depicted in dashed lines)
Figure 8:
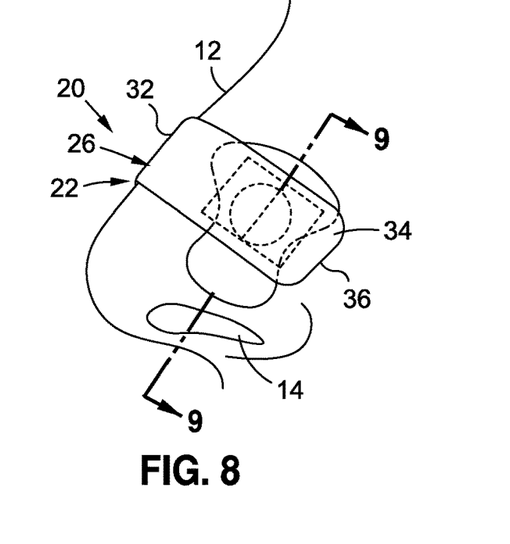
FIG. 8 is a side view of the bridge member and the pair of nasal appliques (depicted in dashed lines) illustrated in FIG. 7.
Figure 9:
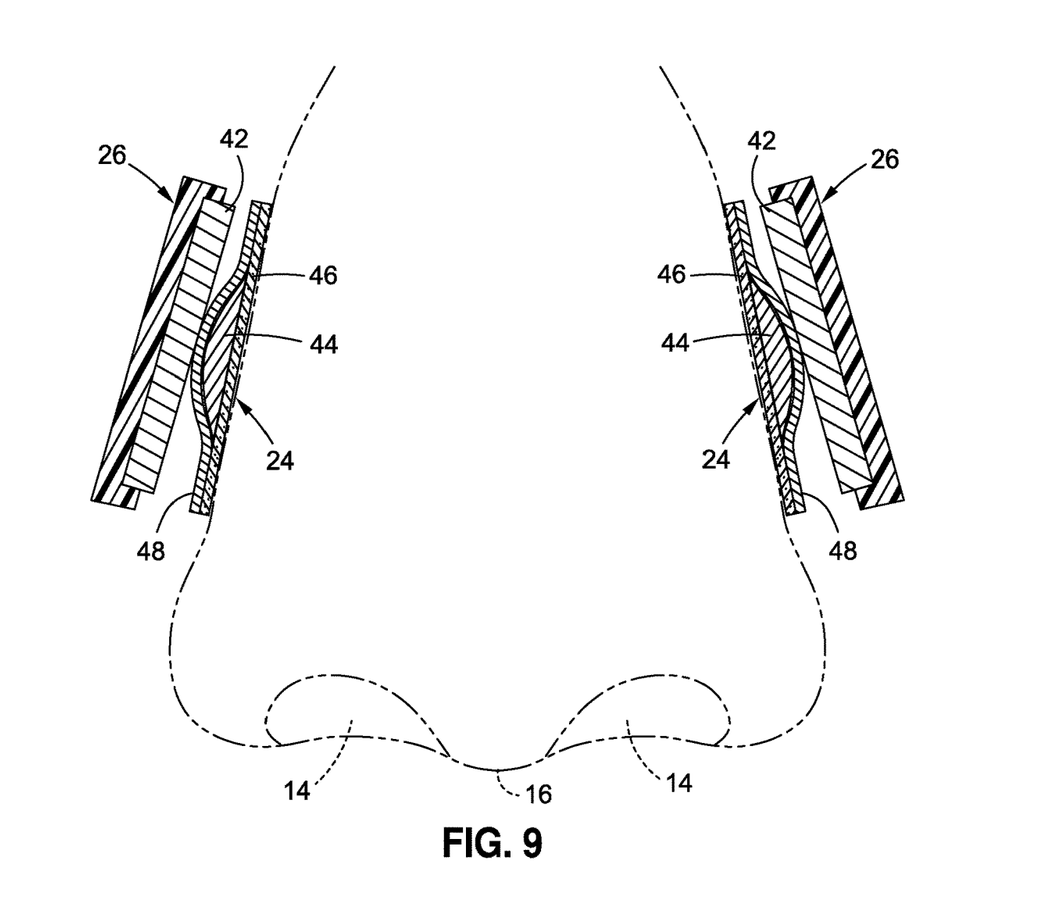
FIG. 9 is a cross sectional view of the bridge member and the pair of nasal appliques taken along line 9-9 depicted in FIG. 8.
Figure 10:
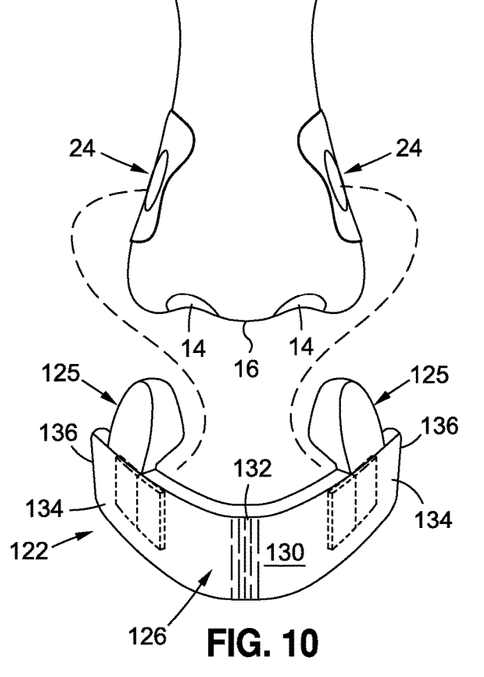
FIG. 10 is an upper perspective view of a second embodiment of a breathing system including a bridge member having a pair of spacers, and a pair of nasal appliques.
Figure 11:
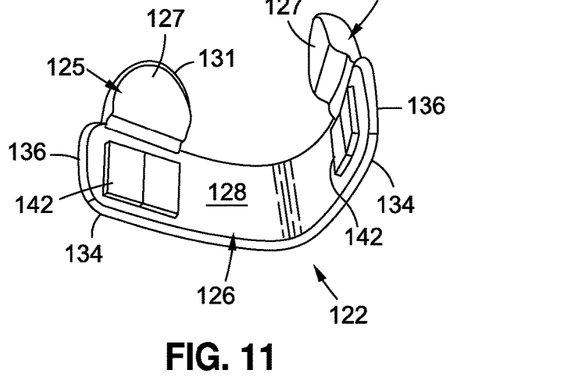
FIG. 11 is a rear perspective view of the bridge member depicted in FIG. 10.
Figure 12:
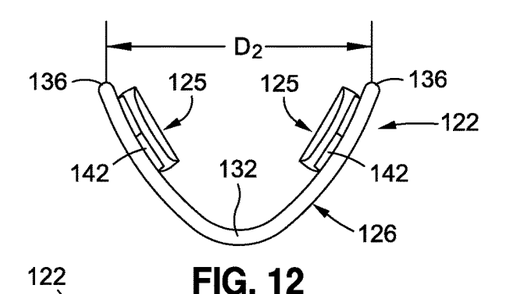
FIG. 12 is a top view of the bridge member depicted in FIG. 10.
Figure 13:
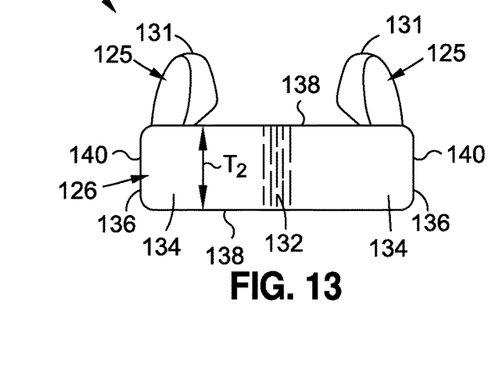
FIG. 13 is a front view of the bridge member depicted in FIG. 10.
Figure 14:
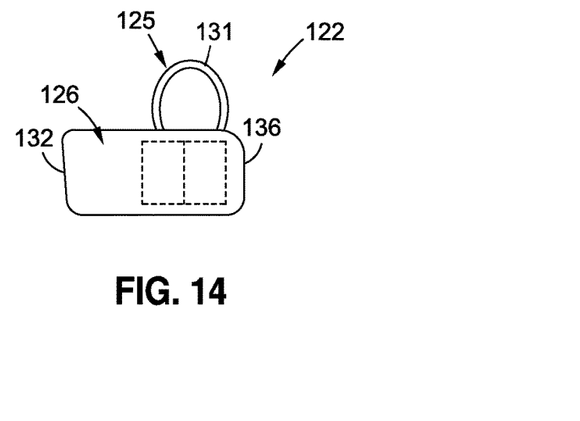
FIG. 14 is a side view of the bridge member depicted in FIG. 10.
Figures 15, 16:
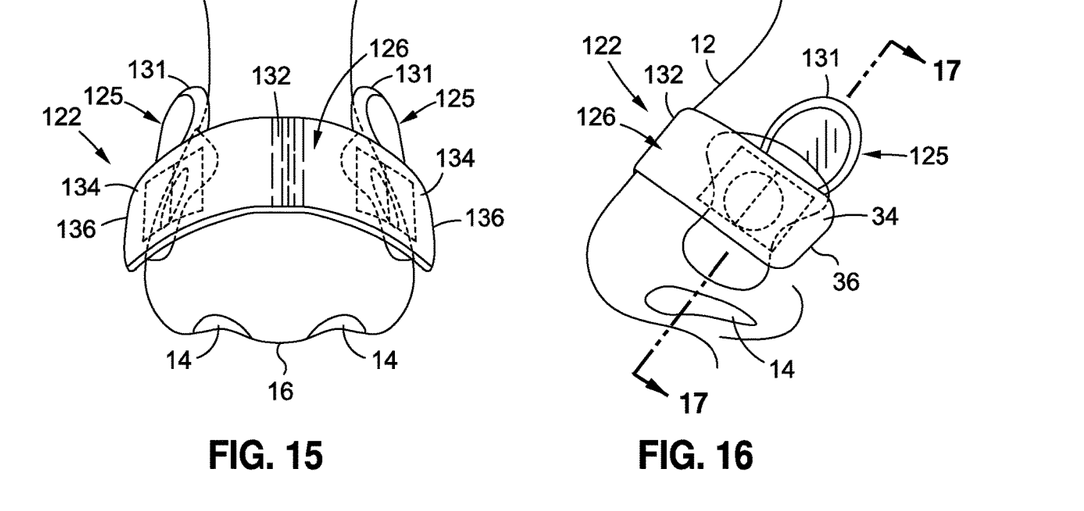
FIG. 15 is an upper perspective view of the bridge member depicted in FIG. 10 engaged with the pair of nasal appliques (depicted in dashed lines)
FIG. 16 is a side view of the bridge member and the nasal applique (depicted in dashed lines) illustrated in FIG. 15.
Figure 17:
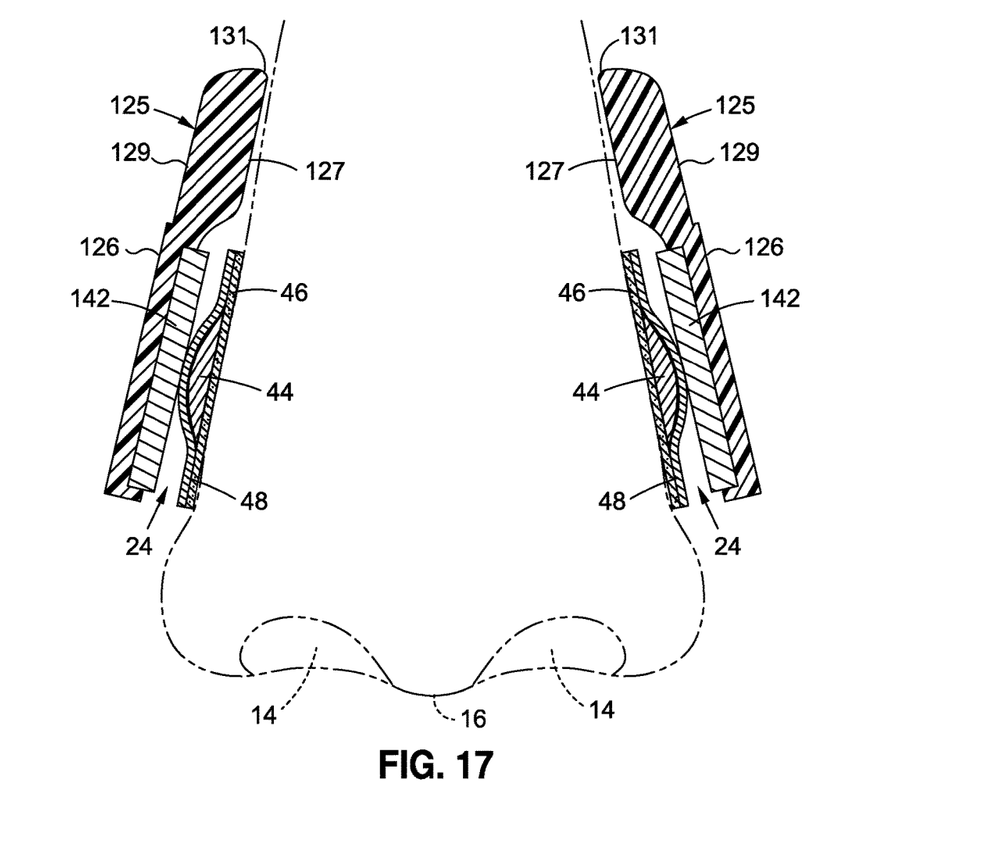
FIG. 17 is a cross sectional view of the bridge member and the pair of nasal appliques taken along line 17-17 depicted in FIG. 16.
Figure 18:
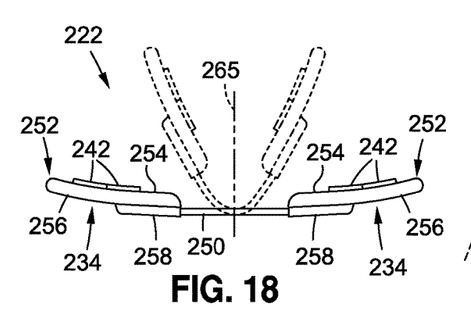
FIG. 18 is a top view of a third embodiment of a bridge member, the bridge member being transitional between a neutral position and a flexed position (depicted in dashed lines)

The bridge member 122 includes an arcuate main body 126 having a concave inner surface 128 and an opposing convex outer surface 130. The main body 126 includes a middle portion 132 defining an apex which is located between two distal portions 134, wherein each distal portion 134 terminates at a respective distal tip 136. The two distal tips 136 are spaced from each other by a distance, $D_2$ which allows the bridge member 122 to fit over the user's nose 10, with the distal portions 134 being positioned adjacent opposing lateral regions 18 of the user's nose 10. The bridge member 122 may be fabricated in various sizes to accommodate differently sized noses, as well as to create different amounts of dilation. Along these lines, the distance $D_2$ may be anywhere from 1.0 inch for use on a small nose (e.g., for a child), to over 2.5 for use on a larger nose. For an average nose, the distance $D_2$ may be approximately equal to 1.75 inches.

The main body 122 includes a pair of opposed longitudinal edges 138 and a pair of opposed transverse edges 140, which essentially define the aforementioned distal tips 136. The distance between the opposed longitudinal edges 140 defines a bridge member thickness, $T_2$, which may be equal to approximately 0.5 inches, although other thickness dimensions may be used without departing from the spirit and scope of the present invention.

The main body 126 is rigidly formed so as to substantially maintain its shape. Along these lines, the main body 126 is preferably more resistant to bending, or flexing than is the skin of the user's nose 10. In this respect, the main body 126 is capable of being disposable in compression, that is to say, the main body 126 is capable of having a force applied thereto.

The bridge member 122 further includes a plurality of magnets 142 coupled to the concave inner surface 128 adjacent the distal portions 134 thereof. In the exemplary embodiment, the bridge member 122 includes a pair of magnets 142 at each distal portion 134. The magnets 142 may be received within a cavity or recess formed within the main body 126 that is substantially complimentary in shape and size to the pair of magnets 142. The magnets 142 may be adhered or otherwise coupled to the main body 126 using fastening mechanisms known by those skilled in the art.

Additionally coupled to the main body 126 at respective distal portions thereof is a pair of spacers 125. Each spacer 125 is located adjacent a respective distal portion 134 of the main body 126 and includes a contact surface 127 and an opposing outer surface 129, wherein the contact surface 127 is adapted to engage with the wearer's nose 10. When viewed from the perspective shown in FIG. 17, which is a cross-sectional view of the breathing system in use on a user's nose 10, shown in phantom, the inner surface 128 of the main body 126 resides between the contact surface 127 of the spacer 125 and the outer surface 130 of the main body 126. In this respect, the contact surface 127 is offset from the inner surface 128.

Each spacer 125 additionally protrudes from the main body 126 beyond one of the longitudinal edges 138 and terminates at a tip 131. In the exemplary embodiment, the spacer 125 defines an arcuate peripheral contour, although it is understood that in other embodiments, the peripheral contour of the spacer 125 may assume any shape or configuration.

During use of the breathing system, the nasal appliques 24 are applied to the user's nose 10, as described above. Once the appliques 24 are applied, the user places the bridge member 122 over the nose 10, with the contact surface 127 of the spacers 125 contacting respective lateral regions 18 of the user's nose 10. As the bridge member 122 is moved closer to the nasal appliques 24, the magnetic attraction between the magnets 142 and the metallic elements 44 pulls the appliques 24 outwardly, thereby imparting a dilating force on the lateral regions 18 of the nose 10, causing the nose 10 to dilate. The presence of the spacer 125 allows the metallic elements 44 to be drawn further to engage with the magnets 142, which enhances the dilating effect.

The bridge member 122 may be disengaged from the nasal appliques 24 by pulling the bridge member 122 away from the appliques 24. Once disengaged, the dilating force is no longer applied to the user's nose 10, thereby allowing the nose 10 to retract and assume its normal position. In this respect, the breathing system may be selective transitioned between an ON state and an OFF state, as described above.

Referring now to FIGS. 18-33, there is depicted several embodiments of bridge members adapted for use with the nasal appliques 24 described above. The bridge members shown in FIGS. 18-33 differ from the bridge members 22, 122 previously shown and described by virtue of the ability of the bridge members shown in FIGS. 18-33 to flex and conform to the anatomy of the user's nose 10. In some instances, the bridge members are flexible and capable of assuming a specific position (see FIGS. 18-25), while other bridge members are flexible between a neutral position and a flexed position, with the bridge members being biased toward the neutral position.

Referring now specifically to FIGS. 18-21, there is depicted a third embodiment of a bridge member 222 which includes a flexible middle portion 232 disposed between a distal members 234. In the exemplary embodiment, the flexible middle portion 232 is comprised of a plurality of flexible bars 250, specifically three bars 250, although the number of bars 250 may vary without departing from the spirit and scope of the present invention. The bars 250 are flexible, and yet are of sufficient rigidity to independently maintain a desired configuration, similar to the ability of a conventional paperclip to be bent and assume a particular configuration, although the bars 250 are preferably of a more rigid stiffness than a conventional paperclip.

Each bar 250 is coupled to each distal member 234 at a respective end portion of the bar. Each distal member 234 includes a main body 252 having an inner surface 254, an opposing outer surface 256, and a set of engagement sleeves 258 coupled to the outer surface 256, wherein the number of engagement sleeves 258 equals the number of bars 250. Thus, in the exemplary embodiment, each main body 252 includes three engagement sleeves 258, wherein each engagement sleeve 258 is specifically adapted to receive one of the bars 250 at a respective end portion thereof. Each main body 252 also defines a distal edge 260, which is spaced away from the bars 250 and extend generally perpendicular to the bars 250. The distal edges define a bridge member length, $L_1$, which may be equal to approximately 2.0-3.0 inches when the bars 250 are generally linear (e.g., when the bridge member 222 is in a generally flat configuration).

Each distal member 234 additionally includes one or more magnets 242 coupled to the main body 252. In the exemplary embodiment, each distal member 234 includes two magnets 242 coupled thereto. The magnets 242 may be received within a recess formed within the main body 252.

Figure 19:
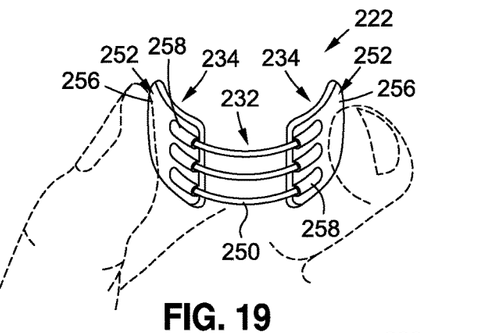
FIG. 19 is an upper perspective view of the bridge member depicted in FIG. 18, the bridge member being shown in a flexed position.
Figure 20:
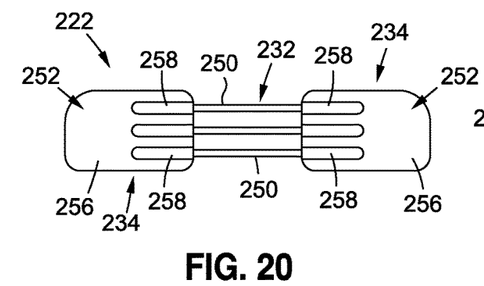
FIG. 20 is a front view of the bridge member depicted in FIG. 18.
Figure 21:
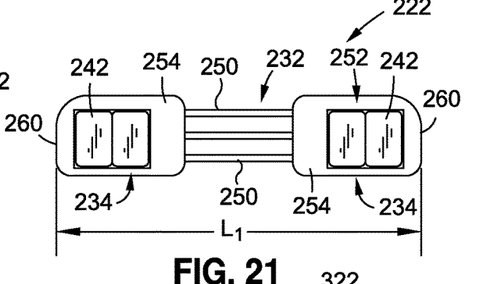
FIG. 21 is a rear view of the bridge member depicted in FIG. 18.
Figure 22:
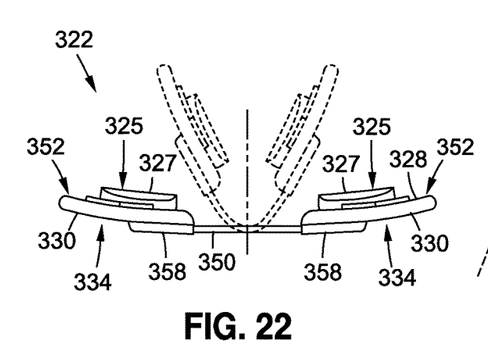
FIG. 22 is a top view of a fourth embodiment of a bridge member being transitional between a neutral position and a flexed position (depicted in dashed lines), wherein the bridge member includes a pair of spaces coupled thereto.
Figure 23:
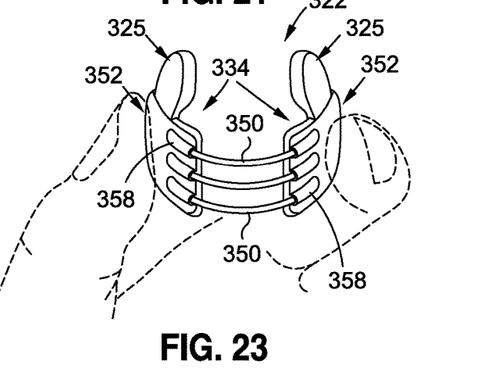
FIG. 23 is an upper perspective view of the bridge member depicted in FIG. 22, the bridge member being shown in a flexed position.
Figure 24:
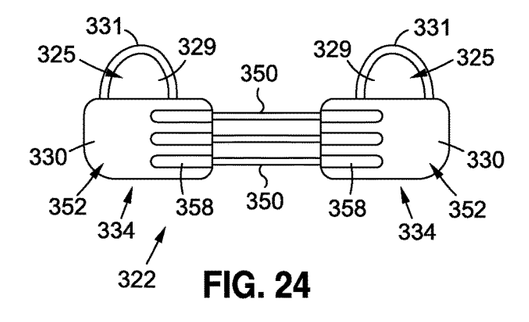
FIG. 24 is a front view of the bridge member depicted in FIG. 22.
Figure 25:
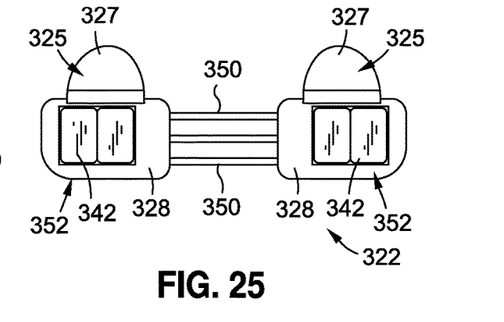
FIG. 25 is a rear view of the bridge member depicted in FIG. 22.
Figure 26:
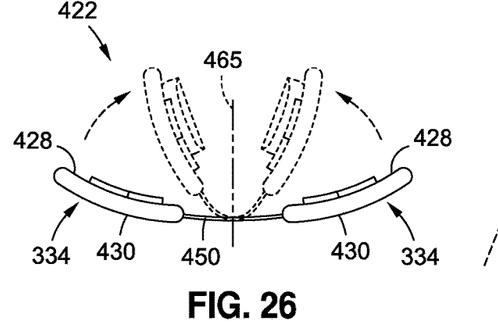
FIG. 26 is a top view of a fifth embodiment of a bridge member being transitional between a neutral position and a flexed position (shown in dashed lines)

The bridge member 222 is configured to be selectively bent or flexed into a prescribed configuration which generally conforms to the anatomy of the user's nose 10. When the bridge member 22 is bent, the bars 250 are bent about a bend axis 265, such that the distal members 234 are moved toward each other and the bend axis 265. FIG. 19 depicts a user's hand (in phantom), pressing the distal members 234 together to bend the bridge member 222 into the desired configuration. As noted above, the bars 250 are preferably configured such that when the bars 250 are bent into the desired configuration, the bars 250 are capable of staying in that desired configuration.

In use, the bridge member 222 is bent or flexed into the prescribed configuration based on the particularly anatomy or configuration of the user's nose 10. Along these lines, the bridge member 222 is bent until the main bodies 252 are spaced slightly farther than the distance between the lateral regions 18 of the user's nose 10. The bridge member 222 will maintain the prescribed, bent configuration due to the mechanical properties of the bars 250.

After the bridge member 222 is bent and the nasal appliques 24 are applied to the nose 10, the bridge member 222 is placed over the user's nose 10, which causes the magnets 242 in the bridge member 222 to interact with the metallic elements 44 in the nasal appliques 24. The interaction imparts a dilating force on the user's nose 10, which in turn opens the nasal passageways 14 to enhance the user's ability to breathe. When the bridge member 222 is placed on the nasal appliques 24, the system is considered to be "active" and in an ON state, whereas when the bridge member 222 is removed from the nasal appliques 24, the system is considered to be "inactive" and in an OFF state.

Referring now to FIGS. 22-25, there is depicted a fourth embodiment of a bridge member 322, which is similar to the bridge member 222 depicted in FIGS. 18-21, although the bridge member 322 includes a pair of spacers 325 coupled to respective ones of the main bodies 352. In particular, the bridge member 322 generally includes a plurality of bars 350, a pair of distal members 334, wherein each distal member 334 includes a main body 352 and a plurality of sleeves 358 which engage with the bars 350, similar to the sleeves described above.

Each spacer 325 is coupled to a respective one of the pair of main bodies 352 and includes a contact surface 327 and an opposing outer surface 329, wherein the contact surface 327 is adapted to engage with the wearer's nose 10. An inner surface 328 of the main body 352 resides between the contact surface 327 of the spacer 325 and an outer surface 330 of the main body 352. In this respect, the contact surface 327 is offset from the inner surface 328.

Each spacer 325 additionally protrudes from the main body 352 beyond one of the longitudinal edges and terminates at a tip 331. In the exemplary embodiment, the spacer 325 defines an arcuate peripheral contour, although it is understood that in other embodiments, the peripheral contour of the spacer 325 may assume any shape or configuration.

The use of the bridge member 322 is similar to the use of the bridge member described above in relation to FIGS. 18-21. However, the presence of the spacers 325 allows the metallic elements 44 to be drawn further to engage with the magnets 342, which enhances the dilating effect.

Referring now to FIGS. 26-29, there is depicted a fifth embodiment of a bridge member 422, which is distinguishable from the bridge members discussed above primarily because of a flexible band 450 which allows the bridge member 422 to flex between a neutral position and a flexed position.

The bridge member 422 includes a flexible middle portion comprised of the flexible band 450. The flexible band 450 is transitional between a neutral position, shown in FIGS. 26, 28 and 29, and a flexed position, shown in FIG. 26 (in phantom) and FIG. 27. The flexible band 450 differs from the flexible bars discussed above because the flexible band 450 is not capable of independently maintaining the flexed position. Rather, the flexible band 450 is biased toward the neutral position, such that when the band 450 is not acted upon by an outside force, the band 450 returns to the neutral position.

The band 450 is coupled to a pair of distal members 434 at a respective end portions of the band 450. Each distal member 434 includes an inner surface 428, an opposing outer surface 430, and an engagement pocket adapted to receive an end portion of the band 450. In the exemplary embodiment, the engagement pocket extends from a medial end of the distal member 434. The inner surface 428 may also include a cutout in communication with the pocket, wherein the cutout is sized to accommodate one or more magnets 442, as described below. Each distal member 434 also defines a distal edge 460, with the pair of distal edges 460 defining a bridge member length $L_2$ therebetween, which may be equal to approximately 2.0-3.0 inches when the band 450 is generally linear (e.g., when the bridge member 422 is in a generally flat configuration). The band 450 may optionally be coated in a soft, flexible material, such as rubber or fabric, to make the bridge member 422 more comfortable to wear.

Each bridge member 422 additionally includes one or more magnets 442 coupled to the distal members 434 and/or the band 450. In the exemplary embodiment, each end portion of the band 450 includes two magnets 442 coupled thereto. As noted above, the magnets 442 are received within a cutout formed in the distal member 434, such that the distal member 434 partially surrounds the magnets 442.

Figure 27:
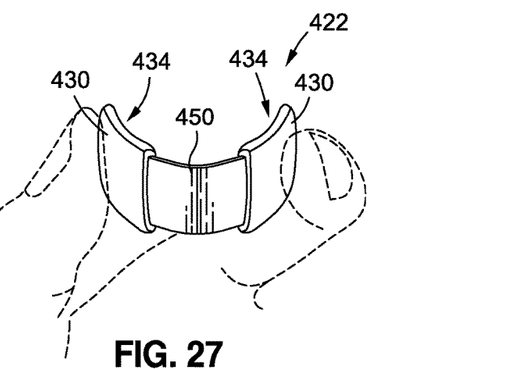
FIG. 27 is an upper perspective view of the bridge member depicted in FIG. 26, the bridge member being shown in a flexed position.
Figure 28:
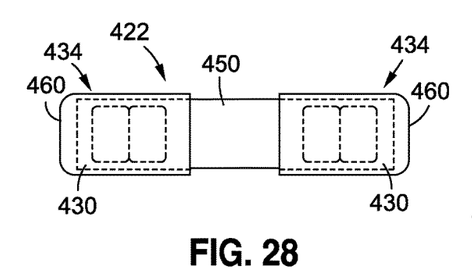
FIG. 28 is a front view of the bridge member depicted in FIG. 26.
Figure 29:
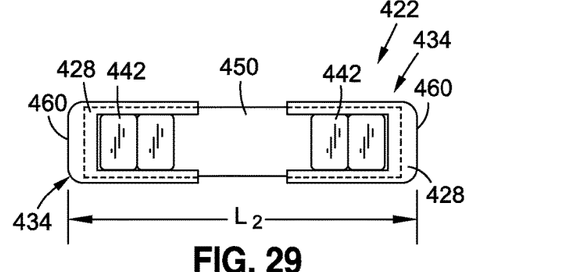
FIG. 29 is a rear view of the bridge member depicted in FIG. 26.
Figure 30:
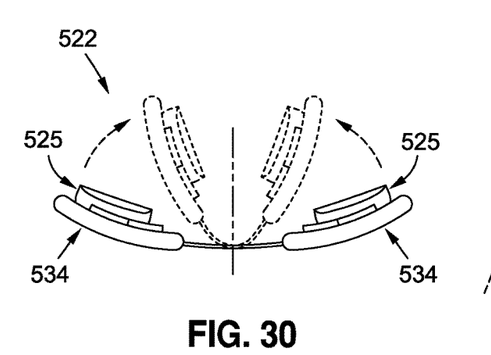
FIG. 30 is a top view of a sixth embodiment of a bridge member being transitional between a neutral position and a flexed position (shown in dashed lines)
Figure 31:
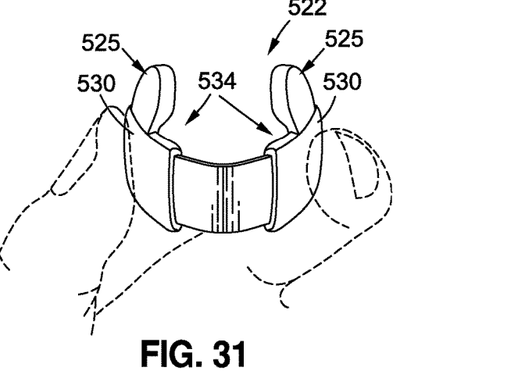
FIG. 31 is an upper perspective view of the bridge member depicted in FIG. 30, the bridge member being shown in a flexed position.
Figure 32:
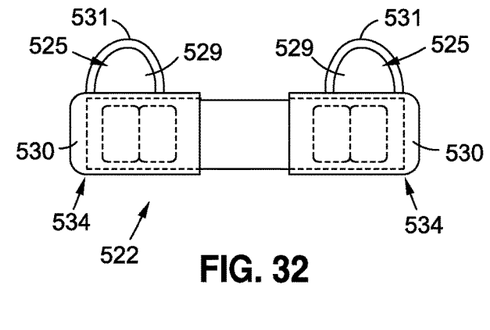
FIG. 32 is a front view of the bridge member depicted in FIG. 30.
Figure 33:
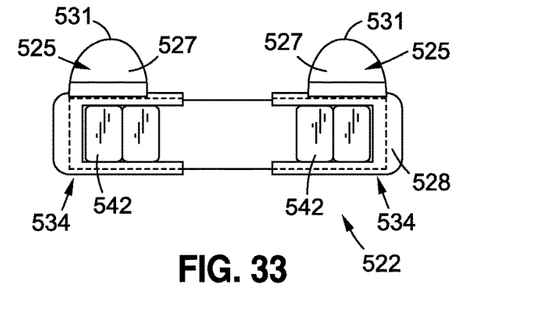
FIG. 33 is a rear view of the bridge member depicted in FIG. 30.

In use, the nasal appliques 224 are applied to the lateral regions 18 of the user's nose 10 and the bridge member 422 is placed over the nasal appliques 24. In particular, the band 450 is bent or flexed to generally conforms to the anatomy of the user's nose 10. When the band 450 is bent, the band 450 bends about a bend axis 465, such that the distal members 434 are moved toward each other and the bend axis 465. FIG. 27 depicts a user's hand (in phantom), pressing the distal members 434 together to bend the bridge member 422. As the bridge member 422 is moved closer to the nasal appliques 24, the magnets 442 in the bridge member 422 interact with the metallic elements 44 in the nasal appliques 24. The magnetic attraction accomplishes two purposes: the first purpose is that the nasal appliques 24 are drawn toward the magnets 442, which imparts a dilating force on the nose 10 causing the nasal passageways 14 to open; the second purpose is that the magnetic attraction maintains the bridge member 422 in the flexed configuration. As noted above, the bridge member 422 is biased toward the neutral position.

Optionally, the biasing force may be strong enough to further dilate the user's nose 10.

The bridge member 422 is configured to selectively transition the breathing system between ON (e.g., active) and OFF (e.g., inactive) states by simply engaging or disengaging the bridge member 422 with the nasal appliques 24, similar to the bridge members discussed above.

Referring now to FIGS. 30-33, there is depicted a sixth embodiment of a bridge member 522, which is similar to the bridge member 422 discussed above, although the bridge member 522 includes a pair of spacers 525 coupled to respective ones of the distal members 534. In particular, the bridge member 522 generally includes a flexible band 550, a pair of distal members 534, wherein each distal member 534 includes a pocket configured to engage with the band 550.

Each spacer 525 is coupled to a respective one of the pair of distal members 534 and includes a contact surface 527 and an opposing outer surface 529, wherein the contact surface 527 is adapted to engage with the wearer's nose 10. The inner surface 528 of the distal member 534 resides between the contact surface 527 of the spacer 525 and the outer surface 530 of the distal member 534. In this respect, the contact surface 527 is offset from the inner surface 528.

Each spacer 525 additionally protrudes from the distal member 534 beyond one of the longitudinal edges and terminates at a tip 531. In the exemplary embodiment, the spacer 525 defines an arcuate peripheral contour, although it is understood that in other embodiments, the peripheral contour of the spacer 525 may assume any shape or configuration.

The use of the bridge member 522 is similar to the use of the bridge member 422 described above in relation to FIGS. 26-29. However, the presence of the spacers 525 allows the metallic elements 44 to be drawn out further to engage with the magnets 542, which enhances the dilating effect.

Figure 34:
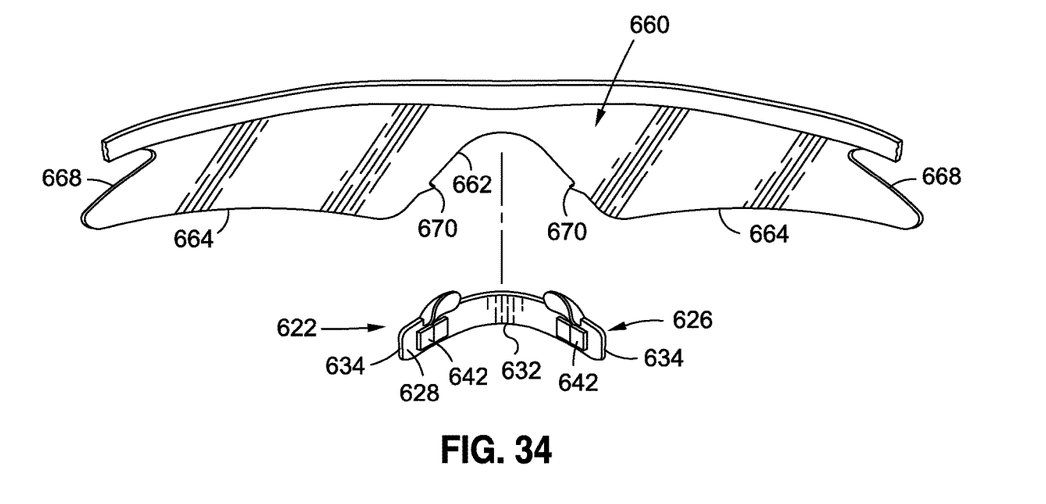
FIG. 34 is a rear view of a seventh embodiment of a bridge member adapted to interface with eyewear, the bridge member being disengaged from the eyewear.
Figure 35:
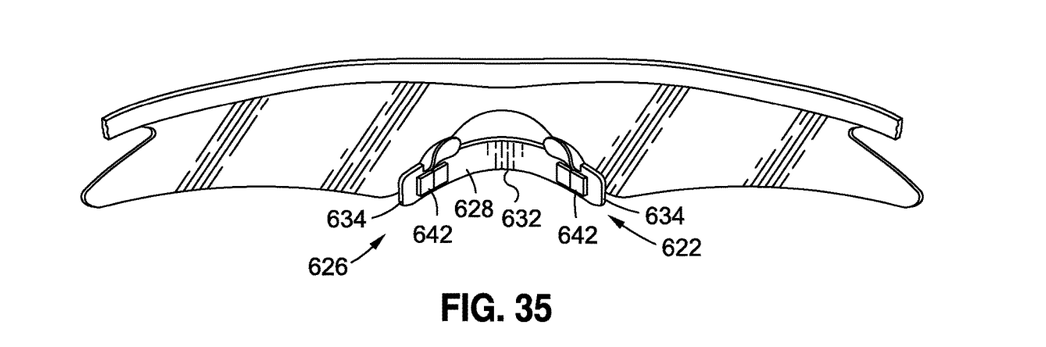
FIG. 35 is a rear view of the bridge member depicted in FIG. 34, the bridge member being engaged with the eyewear.
Figure 36:
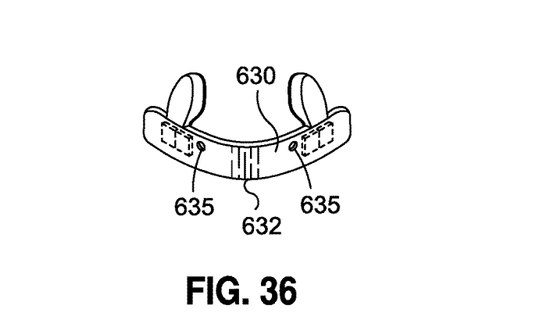
FIG. 36 is a front upper perspective view of the bridge member depicted in FIGS. 34 and 35.

Referring now to FIGS. 34-36, there is depicted a seventh embodiment of a bridge member 622 that is specifically configured and adapted to not only interface with nasal appliques 24, but is also adapted to interface with a lens 660, such as a glasses lens, goggle lens, or other optical lens. The interaction between the bridge member 622 and the lens 660 may be sufficient to stabilize the lens on the user's nose to allow the lens 660 to reside over the wearer's eyes without the use of a support strap or arms, as are commonly employed with goggles and glasses frames, respectively. In particular, the lens 660 includes a peripheral edge defining a bridge section 662 and a pair of lower sections 664, with each lower section 664 transitioning to a respective side section 668. The bridge section 662 may include a pair of tabs 670 for engaging with the bridge member, as will be described in more detail below.

The bridge member 622 includes a main body 626 having a concave inner surface 628 and a convex outer surface 630. The bridge member 622 defines a middle portion 632 and a pair of distal portions 634. Attached to each distal portion 634 is at least one magnet 642. The magnet 642 may reside within a recess which extends into the main body 626 from the concave inner surface 630. The bridge member 622 may further include a lens receiving recess or opening 635 extending into the bridge member 622 from the convex outer surface 628. The lens receiving opening 635 may be adapted to receive respective ones of the tabs 670 for connecting the lens 660 to the bridge member 622.

The bridge member 622 may be selectively transitioned relative to the lens between a disengaged configuration (see FIG. 34) and an engaged configuration (see FIG. 35). The user may engage the bridge member 622 with the lens 660 by pressing the convex outer surface 630 against the bridge section 662 of the lens 660, until the bridge section 662 is received within the lens receiving opening 635 (as shown in FIG. 35).

The bridge member-lens assembly may be attached to the user's nose 10 via the nasal appliques 24. In particular, as the bridge member 622 is moved closer to the nasal appliques 24, the magnets 642 in the bridge member 622 interact with the metallic elements 44 in the nasal appliques 24, such that the magnetic force therebetween holds the lens 660 in place over the user's nose 10. Furthermore, the magnetic attraction also imparts a dilating force on the user's nose 10 causing the nasal passageways 14 to open for enhancing the user's ability to breathe.

While FIGS. 34-36 show bridge member 622 as being adapted to for use in stabilizing and securing the lens 660 in place on the user, it is understood that any one of the foregoing embodiments of the bridge member described above and shown in the Figures may be adapted for use with the lens 660.

Although the foregoing describes the nasal appliques 24 as including the metallic elements, and the magnets as being part of the bridge member, it is understood that in other embodiments, the location of the magnets and metallic elements may be reversed. In particular, the metallic elements may be part of the bridge member and the magnets may be part of the nasal appliques. Alternatively, it is also understood that the metallic elements may be replaced with magnets, such that both the bridge members and nasal appliques have magnets which are polar opposites, and thereby are attracted to each other.

The particulars shown herein are by way of example only for purposes of illustrative discussion, and are not presented in the cause of providing what is believed to be most useful and readily understood description of the principles and conceptual aspects of the various embodiments of the present disclosure. In this regard, no attempt is made to show any more detail than is necessary for a fundamental understanding of the different features of the various embodiments, the description taken with the drawings making apparent to those skilled in the art how these may be implemented in practice.

What is claimed is:

1. A breathing system adapted to open a nasal passage of a user's nose, the breathing system comprising:
   a bridge member having a pair of distal portions, a middle portion positioned between the pair of distal portions, and an inner surface that defines a concave configuration, the bridge member being configured to be positionable adjacent the user's nose, with the inner surface facing the user's nose and each distal portion residing adjacent a respective lateral region of the user's nose; and
   at least one nasal applique adapted to be attachable to a respective lateral region of the user's nose, each nasal applique being magnetically attractable to a respective one of the pair of distal portions, the attraction between the at least one nasal applique and the bridge member imparting a dilating force on the user's nose to dilate the nasal passage;
   the bridge member being of sufficient rigidity so as to retain the concave configuration of the inner surface when the bridge member is detached from the at least one nasal applique.

2. The breathing system recited in claim 1, wherein each nasal applique includes:

a flexible base layer including a first surface and an opposing second surface, the first surface having an adhesive disposed thereon to enable the first surface to be selectively attachable to the nose of the user; and a metallic element coupled to the second surface of the base layer.

3. The breathing system recited in claim 2, wherein the bridge member includes a main body and a pair of magnets coupled to the main body at respective ones of the distal portions of the bridge member, the metallic element in each nasal applique being magnetically attractable to a respective one of the pair of magnets and having an arcuate surface over which the respective one of the pair of magnets is moveable when the metallic element is magnetically coupled to the respective one of the pair of magnets.

4. The breathing system recited in claim 1, wherein the bridge member includes:

a first surface and an opposing second surface, the first surface facing toward the user's nose and the second surface facing away from the user's nose when the bridge member is positioned adjacent the user's nose; and a pair of spacers extending from the first surface and away from the second surface, each spacer being positioned at a respective one of the pair of distal portions.

5. The breathing system recited in claim 4, wherein the pair of spacers are integrally formed with the main body.

6. The breathing system recited in claim 1, wherein the bridge member is resistant to bending when attached to the at least one nasal applique.

7. The breathing system recited in claim 1, wherein the bridge member is adapted to be attachable to eyewear.

8. A breathing system attachable to a nose of a user for selectively dilating comprising:

at least one nasal applique configured to be attachable to an outer surface of a user's nose; and a bridge member having an inner surface that is of a concave configuration, the bridge member being configured to be selectively positionable adjacent the nose of the user such that the inner surface faces the nose of the user and to magnetically interact with the at least one nasal applique, the bridge member being of sufficient rigidity so as to retain the concave configuration of the inner surface when the bridge member is disengaged from the at least one nasal applique;

the at least one nasal applique and the bridge member being configured to selectively transition between an ON state wherein the at least one nasal applique interacts with the bridge member to apply a dilating force on the nose of the user, and an OFF state wherein the bridge member is moved away from the at least one nasal applique to cease application of the dilating force on the nose of the user.

9. The breathing system recited in claim 8, wherein the bridge member includes a main body and a pair of magnets coupled to the main body at respective ones of the distal portions of the bridge member, the metallic element in each nasal applique being magnetically attractable to a respective one of the pair of magnets.

10. The breathing system recited in claim 8, wherein the bridge member is resistant to bending when attached to the at least one nasal applique.

11. A bridge member adapted for use with a pair of nasal appliques to dilate a nose of a user, the bridge member comprising:

an arcuate main body having a pair of distal portions, a middle portion defining an apex, and an inner surface that is of a concave configuration, with each distal portion being located on a respective side of the apex;

the main body being configured to be positionable over the nose of the user to assume a first position wherein the pair of distal portions of the main body extend over opposed regions of the nose of the user;

the pair of distal portions being magnetically interactable with respective ones of the pair of nasal appliques when the pair of nasal appliques are coupled to the nose of the user and the main body is in the first position to cause dilation of the nose of the user;

the main body being of sufficient rigidity so as to retain the concave configuration of the inner surface when the main body is disengaged from the pair of nasal appliques.

12. The bridge member recited in claim 11, further comprising at least two magnets coupled to the main body and positioned at respective ones of the pair of distal portions.

13. The bridge member recited in claim 12, wherein each distal portion extends from the apex to define a respective distal tip, the at least two magnets being spaced from the distal tips.

14. The bridge member recited in claim 11, further comprising a first pair of magnets coupled to the main body at a first one of the pair of distal portions and a second pair of magnets coupled to the main body at a second one of the pair of distal portions.

15. The bridge member recited in claim 11, each distal portion extends away from the apex to define a distal tip, wherein the distal tips of the distal portions are spaced from each other by 1.0-2.5 inches.

16. The bridge member recited in claim 11, wherein the main body includes a pair of opposed longitudinal edges spaced apart from each other by approximately 0.5 inches.

17. The bridge member recited in claim 11, wherein the main body is capable of being selectively transitioned between an ON state and an OFF state, the main body being magnetically engaged with the pair of nasal appliques to impart the dilating force on the nose of the user when the main body is in the ON state and the main body being magnetically disengaged from the pair of nasal appliques to cease imparting of the dilating force on the nose of the user.

18. The bridge member recited in claim 11, wherein the main body is adapted to be attachable to eyewear.

* * * * *